United States Patent
Chugh et al.

(10) Patent No.: US 11,254,944 B2
(45) Date of Patent: Feb. 22, 2022

(54) AGROBACTERIUM DERIVED CELL PENETRATING PEPTIDES AS NANOCARRIERS

(71) Applicant: INDIAN INSTITUTE OF TECHNOLOGY DELHI, New Delhi (IN)

(72) Inventors: Archana Chugh, New Delhi (IN); Aastha Jain, New Delhi (IN); Mudit Mishra, New Delhi (IN)

(73) Assignee: INDIAN INSTITUTE OF TECHNOLOGY DELHI, New Delhi (IN)

( * ) Notice: Subject to any disclaimer, the term of this patent is extended or adjusted under 35 U.S.C. 154(b) by 158 days.

(21) Appl. No.: 16/595,009

(22) Filed: Oct. 7, 2019

(65) Prior Publication Data

US 2020/0095283 A1    Mar. 26, 2020

Related U.S. Application Data (63) Continuation-in-part of application No. PCT/IN2017/050331, filed on Aug. 8, 2017.

(30) Foreign Application Priority Data

Apr. 7, 2017 (IN) .............. 201711012666

(51) Int. Cl.
| | |
|---|---|
| *C07K 4/04* | (2006.01) |
| *C12N 15/82* | (2006.01) |
| *A61K 47/64* | (2017.01) |
| *C07K 7/08* | (2006.01) |
| *C12N 15/10* | (2006.01) |
| *A01N 63/50* | (2020.01) |

(52) U.S. Cl.
CPC ......... *C12N 15/8201* (2013.01); *A01N 63/50* (2020.01); *A61K 47/6415* (2017.08); *C07K 4/04* (2013.01); *C07K 7/08* (2013.01); *C12N 15/102* (2013.01); *C12N 15/8205* (2013.01)

(58) Field of Classification Search
CPC .............. C12N 15/8201; C12N 15/102; C12N 15/8205; C12N 15/87; A01N 63/50; A61K 47/6415; C07K 4/04; C07K 7/08; C07K 14/195
See application file for complete search history.

(56) References Cited

U.S. PATENT DOCUMENTS

| | | | | |
|---|---|---|---|---|
| 7,314,737 B2 * | 1/2008 | Hooykaas | ............ | C07K 14/195 435/320.1 |
| 2012/0070900 A1 | 3/2012 | Kovalchuk et al. | | |

OTHER PUBLICATIONS

Futaki et al, The Journal of Biological Chemistry, Feb. 23, 2001, vol. 276, No. 8, 5836-5840 (Year: 2001).*
Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Mysore et al (MPMI, vol. 11, No. 7, 1998, 668-683) (Year: 1998).*
International Search Report for PCT/IN2017/050331; Applicant: Indian Institute of Technology Delhi, International Filing Date: Aug. 8, 2017, 5 pages, Nov. 15, 2017.
Written Opinion for PCT/IN2017/050331; Applicant: Indian Institute of Technology Delhi, International Filing Date: Aug. 8, 2017, 6 pages, dated Nov. 15, 2017.
First Examination Report for related Indian Application No. 201711012666, 8 pages, dated Oct. 31, 2019.
Chugh, et al., "Cell-Penetrating Peptides: Nanocarrier for Macromolecule Delivery in Living Cells," IUBMB Life, 62(3): pp. 183-193, Mar. 2010.
Chugh, Archana and Eudes, Francois, "Study of uptake of cell penetrating peptides and their cargoes in permeablized wheat immature embryos," the FEBS Journal 275, pp. 2403-2414 (2008).
Ziemienowicz, et al., "A Novel Method of Transgene Delivery into Triticale Plants Using the Agrobacterium Transferred DNA-Derived Nano-Complex [W][OA]," Plant Physiology(R), American Society of Plant Biologists, vol. 158, pp. 1503-1513, Apr. 2012.
Torchilin, Vladimir P., "Cell Penetrating Peptide-Modified Pharmaceutical Nanocarriers for Intracellular Drug and Gene Delivery," Biopolymers (Peptide Science), vol. 90, No. 5, pp. 604-610, (2008).
Howard, et al., "The VirD2 Protein of A. tumefaciens Contains a C-Terminal Bipartite Nuclear Localization Signal: Implications for Nuclear Uptake of DNA in Plant Cells," Cell, vol. 68, pp. 109-118, Jan. 10, 1992.
Intellectual Property India, Government of India, Hearing Notice in related Indian patent application No. 201711012666, 3 pages, dated Oct. 12, 2021.
Herrera-Estrella, et al., A bacterial peptide acting as a plant nuclear targeting signal: The amino-terminal portion of Agrobacterium VirD2 protein directs a ß-galactosidase fusion protein into tobacco nuclei, Proc. Natl. Acad. Sci. USA, vol. 87(24), pp. 9534-9537, Dec. 1990, Cell Biology.

* cited by examiner

*Primary Examiner* — Sudhakar Katakam
(74) *Attorney, Agent, or Firm* — Dilworth IP, LLC (57) ABSTRACT

The present invention relates to a nanocarrier peptide sequence (SEQ ID NO: 6 KXPXXXXA/V/GXGNXX; wherein X is selected from amino acid R, K, A or H. The present invention also relates to the method for cellular delivery, by implementing the steps of: complexation of a peptide nanocarrier sequence: KXPXXXXA/V/GXGNXX; where X is selected from amino acid R,K,A and H having SEQ ID NO: 6 with a macromolecule to obtain a complex; and administering the complex to a targeted mammalian or plant cell or tissue.

8 Claims, 8 Drawing Sheets
Specification includes a Sequence Listing.

Amino acid sequence analysis (VirD2 and VirE2)

Prediction of CPP activity of "KRPR" and "RARGNRR" individually and together by CellPPD Chemical synthesis, labeling and characterization of Vir peptide

```
SEQUENCE LISTING

<160> NUMBER OF SEQ ID NOS: 10

<210> SEQ ID NO 1
<211> LENGTH: 4
<212> TYPE: PRT
<213> ORGANISM: Agrobacterium tumefaciens

<400> SEQUENCE: 1

Lys Arg Pro Arg
1

<210> SEQ ID NO 2
<211> LENGTH: 9
<212> TYPE: PRT
<213> ORGANISM: Agrobacterium tumefaciens

<400> SEQUENCE: 2

Arg Lys Arg Ala Arg Gly Asn Arg Arg
1               5

<210> SEQ ID NO 3
<211> LENGTH: 13
<212> TYPE: PRT
<213> ORGANISM: Agrobacterium tumefaciens

<400> SEQUENCE: 3

Lys Arg Pro Arg Arg Lys Arg Ala Arg Gly Asn Arg Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Pro Ala Arg Lys Arg Ala Arg Gly Asn Arg Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Lys Arg Pro Arg Arg Lys Ala Ala Ala Gly Asn Arg Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg, Lys, Ala or His
<220> FEATURE:
<221> NAME/KEY: MOD_RES
<222> LOCATION: (4)..(7)
<223> OTHER INFORMATION: Arg, Lys, Ala or His
<220> FEATURE:
<221> NAME/KEY: MOD_RES
<222> LOCATION: (8)..(8)
<223> OTHER INFORMATION: Ala, Val or Gly
<220> FEATURE:
<221> NAME/KEY: MOD_RES
<222> LOCATION: (9)..(9)
<223> OTHER INFORMATION: Arg, Lys, Ala or His
<220> FEATURE:
<221> NAME/KEY: MOD_RES
<222> LOCATION: (12)..(13)
<223> OTHER INFORMATION: Arg, Lys, Ala or His

<400> SEQUENCE: 6

Lys Xaa Pro Xaa Xaa Xaa Xaa Xaa Xaa Gly Asn Xaa Xaa
1               5                   10

<210> SEQ ID NO 7
<211> LENGTH: 5
<212> TYPE: PRT
<213> ORGANISM: Agrobacterium tumefaciens

<400> SEQUENCE: 7

Arg Lys Arg Ala Arg
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ala Pro Ala
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Lys Ala Ala Ala
1               5
```

```
<210> SEQ ID NO 10
<211> LENGTH: 7
<212> TYPE: PRT
<213> ORGANISM: Agrobacterium tumefaciens

<400> SEQUENCE: 10

Arg Ala Arg Gly Asn Arg Arg
1               5
```

AGROBACTERIUM DERIVED CELL PENETRATING PEPTIDES AS NANOCARRIERS

SEQUENCE LISTING

The instant application contains a Sequence Listing which has been filed electronically in ASCII format and is hereby incorporated by reference in its entirety. Said ASCII copy, created on Apr. 3, 2020, is named 435-002US_SL.txt and is 2,564 bytes in size.

TECHNICAL FIELD OF THE INVENTION

The present invention generally relates to agrobacterium derived cell and tissue penetrating peptides as nanocarriers. More particularly, the present invention relates to an antimicrobial peptide based nanocarrier, derived from the virulence factor proteins of *Agrobacterium tumefaciens*, exhibiting cytosolic and nuclear localization.

BACKGROUND OF THE INVENTION

Genetic transformation of the living cells to obtain varieties with desired qualitative traits has been known in the prior art. The genetic manipulation through recombinant DNA methods is of significance to the agriculture sector and biopharmaceutical industry, since plants not only fulfill our daily food requirements but also act as potential systems for production of human therapeutics. In the agriculture sector, genetic modification of crops can confer resistance to plants from abiotic (salinity, drought, extreme temperature) and biotic stress (infestation by insects and pathogens), thereby enhancing their rate of survival and increasing the harvest (Key S et al. 2008).

A known method in the prior-art for modifying the plant genome is the delivery of appropriate genes, proteins or siRNA inside the cells using biological transformation through plasmids and vectors. A common biological transformation method for genetic manipulation in the prior art employs *Agrobacterium tumefaciens* as a vector for gene delivery (Rogers S G et al. 1986). The Vir proteins or virulence factors of *Agrobacterium tumefaciens* shows a collective function to excise the T-DNA region of the Ti plasmid and its transfer and integration in the plant genome. Amongst all the Vir proteins, VirD2 is involved in localization of T-DNA to the nucleus and its integration into host DNA. VirD2 contains a C-terminal bipartite nuclear localizing sequence (NLS) that serves to direct the complexed T-strand to the plant nucleus (Mysore K S et al. 1998).

Previously, attempts have been made to transfect synthetic T-DNA complexes in mammalian cells using the Vir D2 and E2 proteins (Pelczar P et al. 2004). Further examples of known prior-art teaching use of Vir protein for delivery of appropriate genes, proteins or siRNA inside the cells include: US 20050289667A1 teaching a method of introducing the exogenous DNA inside the cell with the plasmid aided by Vir gene region of the Ti plasmid of the *Agrobacterium tumefaciens*, EP2647715A1 elaborating transient transfection of a plant or leaves of the plant in suspension having *Agrobacterium* cells, and US20120070900A1 discussing deployment of T-DNA protein nano complexes for plant transformation.

Therefore, there is a continued need in the art for improving penetration of Vir proteins (peptide carrier) and improved translocation of the cargo proteins in the plant tissues without use of additional transfection agent.

OBJECTS OF THE INVENTION

The main objective of this invention is to overcome the conventional problems in the prior art.

An object of the present invention is to provide agrobacterium derived cell penetrating peptides as nanocarriers.

Another object of the present invention is to provide novel peptide-based vector for efficiently targeting and delivering macromolecules to cells in a simple, one-step mechanism.

Yet another object of the present invention is to provide peptide-based delivery method for efficient translocation of macromolecules such as proteins, plasmid DNA, siRNA and mRNA inside cells for generation of transgenics with special characters including tolerance to biotic and abiotic stress; and for production of therapeutics.

An object of the present invention is to develop a novel antimicrobial agent against several plant pathogens with applications in agriculture sector.

Another object of the present invention is to provide with a cost effective and simple, one-step mechanism for efficient gene expression vector for transforming cells.

Another object of the present invention is to provide a biologically safe method of cell transformation.

An object of the present invention is to provide a peptide carrier complex for cell transformation which leads to stable gene expression in the transformed cells.

An object of the present invention is to provide a peptide carrier complex which enables delivery of non-covalently as well as covalently linked macromolecules such as drugs to cells.

An object of the present invention is to provide a peptide carrier complex which localizes specifically in the nucleus and efficiently binds to DNA molecules in vitro, thereby providing a plausible system for gene delivery to the cells for applications in therapeutics and generation of transgenics.

Yet another object of the present invention is to develop a peptide based delivery system for transmission of DNA of heterologous or homologous origin or of synthetic DNA.

Further, an object of the present invention is to provide with a gene expression vector for studying gene function and genetic manipulation in vivo.

These and other advantages of the present invention will become readily apparent from the following detailed description read in conjunction with the accompanying drawings.

SUMMARY OF THE INVENTION

The following presents a simplified summary of the invention in order to provide a basic understanding of some aspects of the invention. This summary is not an extensive overview of the present invention. It is not intended to identify the key/critical elements of the invention or to delineate the scope of the invention. Its sole purpose is to present some concept of the invention in a simplified form as a prelude to a more detailed description of the invention presented later.

In one aspect, the present invention relates to a nanocarrier peptide sequence (SEQ ID NO: 6): KXPXXXXA/V/GXGNXX; wherein X is selected from amino acid R, K, A or H.

The present invention also relates to a method for cellular delivery, comprising the steps of: complexation of a peptide nanocarrier sequence: KXPXXXXA/V/GXGNXX; where X is selected from amino acid R, K, A and H having SEQ ID NO: 6 with a macromolecule to obtain a complex; and administering the complex in the concentration range of 0.1 uM to 50 uM to a targeted mammalian or plant cell or tissue at predetermined pH and temperature conditions.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE ACCOMPANYING DRAWINGS

Some of the objects of the invention have been set forth above. These and other objects, features, aspects and advantages of the present invention will become better understood with regard to the following description, appended claims and accompanying drawings where:

FIG. 1: illustrates the method of screening and sequence formation of the virulence factor proteins VirD2 and VirE2. FIG. 1 discloses SEQ ID NOS 1 and 10, respectively, in order of appearance.

DETAILED DESCRIPTION OF THE INVENTION

The following detailed description of the invention is provided to aid those skilled in the art in practicing the present invention. Even so, the following detailed description should not be construed to unduly limit the present invention as modifications and variations in the embodiments discussed herein may be made by those of ordinary skill in the art without departing from the spirit or scope of the present inventive discovery.

Identification of Sequences

```
SEQ ID NO: 1: KRPR

SEQ ID NO: 2: RKRARGNRR

SEQ ID NO: 3: KRPRRKRARGNRR

SEQ ID NO: 4: KAPARKRARGNRR

SEQ ID NO: 5: KRPRRKAAAGNRR

SEQ ID NO: 6: KXPXXXXA/V/GXGNXX; where X =
any basic amino acid (R, K, A, H)
```

Definitions

Nuclear Localization Signal (NLS)—A nuclear localization signal or sequence (NLS) is an amino acid sequence that 'tags' a protein for import into the cell nucleus by nuclear transport. Typically, this signal consists of one or more short sequences of positively charged lysines or arginines exposed on the protein surface. Different nuclear localized proteins may share the same NLS.

Fluorescein isothiocyanate (FITC)—Fluorescein isothiocyanate (FITC) is a derivative of fluorescein used in wide-ranging applications including flow cytometry. FITC is the original fluorescein molecule functionalized with an isothiocyanate reactive group (—N=C=S), replacing a hydrogen atom on the bottom ring of the structure. This derivative is reactive towards nucleophiles including amine and sulfhydryl groups on proteins.

High-Performance Liquid Chromatography (HPLC)—High-performance liquid chromatography is a technique in analytical chemistry used to separate, identify, and quantify each component in a mixture. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column.

Mass Spectrometry (MS)—Mass spectrometry (MS) is an analytical technique that ionizes chemical species and sorts the ions based on their mass to charge ratio. In simpler terms, a mass spectrum measures the masses within a sample. Mass spectrometry is used in many different fields and is applied to pure samples as well as complex mixtures.

According to various aspects of the invention, there is provided a peptide nanocarrier of general formula (SEQ ID NO: 6): KXPXXXXA/V/GXGNXX; where X=any basic amino acid (R, K, A, H). The peptide nanocarrier delivers macromolecules to a nucleus of a cell and binds to a de-oxy ribo nucleic acid (DNA) of the cell. The following description describes various embodiments of the peptide nanocarrier, method of forming the peptide nanocarrier, methods of using the peptide nanocarrier, and methods of testing the performance in use and properties of the peptide nanocarrier.

According to an embodiment of the invention, the peptide nanocarrier is an agrobacterium derived cell penetrating peptide nanocarrier Vir. The agrobacterium derived cell penetrating peptide nanocarrier Vir is formed by combining two nuclear localization signal (NLS) sequences, KRPR (SEQ ID NO: 1) and RKRAR (SEQ ID NO: 7) of Vir D2 proteins that are derived from C-terminal bipartite sequence of the VirD2 protein of *Agrobacterium tumefaciens* and comprises the sequence: KRPRR KRARGNRR (SEQ ID NO: 3). In said embodiment, the peptide nanocarrier has a net positive charge of +9 units.

In an alternative embodiments, the peptide nanocarrier includes mutated versions of VirD2 peptides: M-Vir1 (mutation in "KRPR" (SEQ ID NO: 1)-"KAPA" (SEQ ID NO: 8)) and M-Vir2 (mutation in "RKRAR" (SEQ ID NO: 7)-"RKAAA" (SEQ ID NO: 9)). The mutated versions are created by substituting the arginine residues with alanine. The resulting peptide nanocarrier may have the following sequences:

SEQ ID NO: 4: KAPARKRARGNRR

SEQ ID NO: 5: KRPRRKAAAGNRR

In general, alternative embodiments of the peptide nanocarrier with mutated Vir peptides may generally include the sequence:
SEQ ID NO: 6: KXPXXXXA/V/GXGNXX; where X=any basic amino acid (R, K, A, H).

According to some aspects of the invention, there is provided a method for making the above-mentioned peptide nanocarrier.

Figure 1:
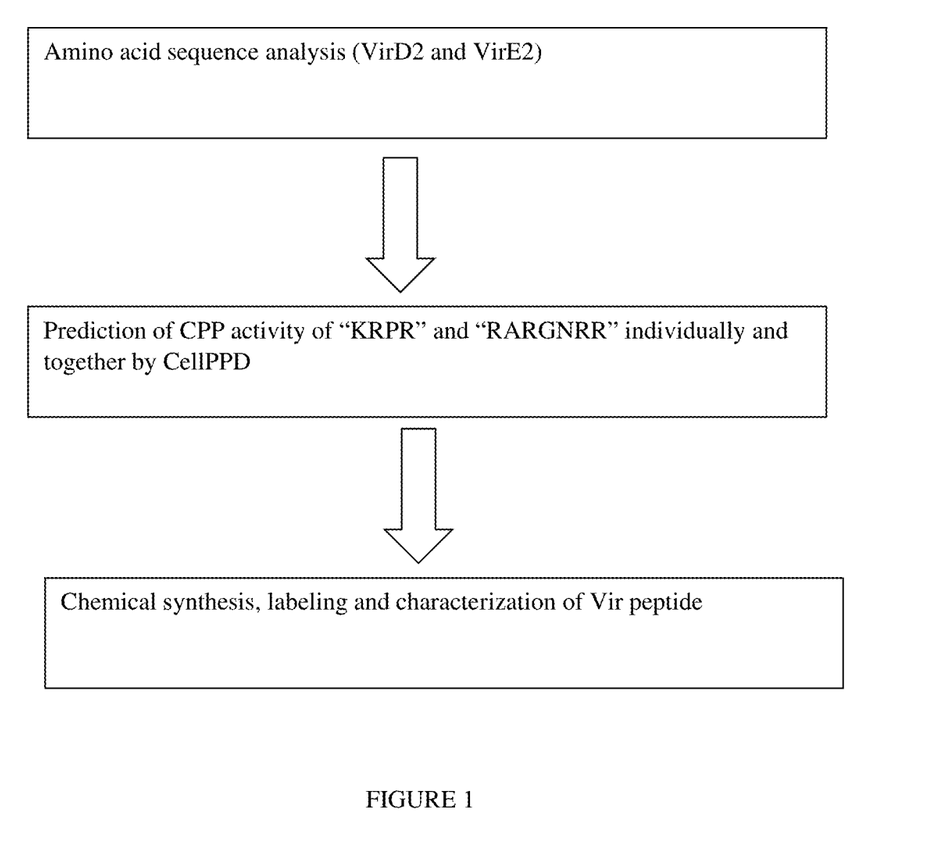

In an embodiment, the method for making the cell penetrating peptide nanocarrier includes selecting two nuclear localization signal (NLS) amino acid sequences, KRPR (SEQ ID NO: 1) and RKRAR (SEQ ID NO: 7) of virulence factor protein VirD2 that are derived from C-terminal bipartite sequence of the VirD2 protein of *Agrobacterium tumefaciens*. The method further includes screening of amino acid sequence of virulence factor proteins VirD2 and VirE2 for presence of "basic amino acid domain" since basic amino acids, particularly Arg (R) and Lys (K) play a crucial role in conferring cell penetration activity to a peptide (Herce et al 2007). After screening, chemically synthesizing the cell penetrating peptide nanocarrier Vir by solid-phase peptide synthesis, labeling the cell penetrating peptide nanocarrier Vir with the fluorophore fluorescein isothiocyanate (FITC) at the N-terminus, purifying the cell penetrating peptide nanocarrier Vir via high-performance liquid chromatography (HPLC), and characterizing the cell penetrating peptide nanocarrier Vir by mass spectrometry (MS) as illustrated in FIG. 1.

According to some aspects of the invention, the said peptide nanocarrier is used in a peptide-based delivery method for efficient translocation of macromolecules such as proteins, plasmid DNA, siRNA and mRNA inside a cell. The method for cellular delivery, comprising the steps of:

complexation of a peptide nanocarrier sequence: KXPXXXXA/V/GXGNXX; where X is selected from amino acid R, K, A and H having SEQ ID NO: 6 with a macromolecule to obtain a complex;

administering the complex in the concentration range of 0.1 uM to 50 uM to a targeted mammalian or plant cell or tissue at predetermined pH and temperature conditions.

The predetermined conditions pH of are in range of 5.5-7.5 and temperature in the range of 18-37 degrees. In some embodiments, the said peptide nanocarrier is used in a peptide-based delivery method for efficient translocation of macromolecules is selected form the group consisting of a peptide, a polypeptide, or a protein, a polysaccharide, a lipid, a lipoprotein, a glyco lipid, a nucleic acid, a molecule drug or a toxin or an imaging or contrast agent inside a cell for generation of transgenics with special characters including tolerance to biotic and abiotic stress.

The following are some exemplary embodiments describing a method of targeting and delivering macromolecules to cells using the agrobacterium derived cell penetrating peptide nanocarrier comprising the sequence: KRPRR KRARGNRR (SEQ ID NO: 3).

In one such embodiment, a method for targeting and delivering macromolecules to mesophyll protoplasts of *T. aestivum* (wheat plant) using the peptide nano carrier includes incubating the mesophyll protoplasts of *T. aestivum* with the peptide nanocarrier.

In the said embodiment, a process for identification of optimum concentration and mechanism of cellular uptake of Vir of the peptide nano-carrier in the mesophyll protoplasts of *T. aestivum* is described below and illustrated in FIG. 2 by employing several endocytic inhibitors such as sodium azide, nocodazole, cytochalasin-D cytochalasin D, and chlorpromazine for blocking different energy-dependent pathways.

The said peptide nanocarrier are incubated with increasing concentrations (5-30 μM) of Fluorescein isothiocyanate (FITC)-Vir to derive an optimum concentration, at which peptide nanocarrier displays sufficient uptake and minimal cytotoxicity to cells. It is observed that with increasing concentration, the number of cells internalizing the peptide also increases proportionally. At 41.1\4 10-15% cells show uptake while at 1504, the number of cells exhibiting cellular uptake increase to 50-60% with distinct nuclear localization. As illustrated in FIG. 2, cellular internalization of FITC-Vir in mesophyll protoplasts of *T. aestivum* is exemplified.

(A) Confocal microscopic images of cellular uptake
(a) untreated (No peptide)
(b) Vir (15 μM)
(c) Tat (5 μM)
(d) M-Tat (5 μM)
(e) Dextran Sulphate (5 μM).
(B) Quantitative estimation of uptake in protoplasts as assessed by fluorimetry.

Figure 2:
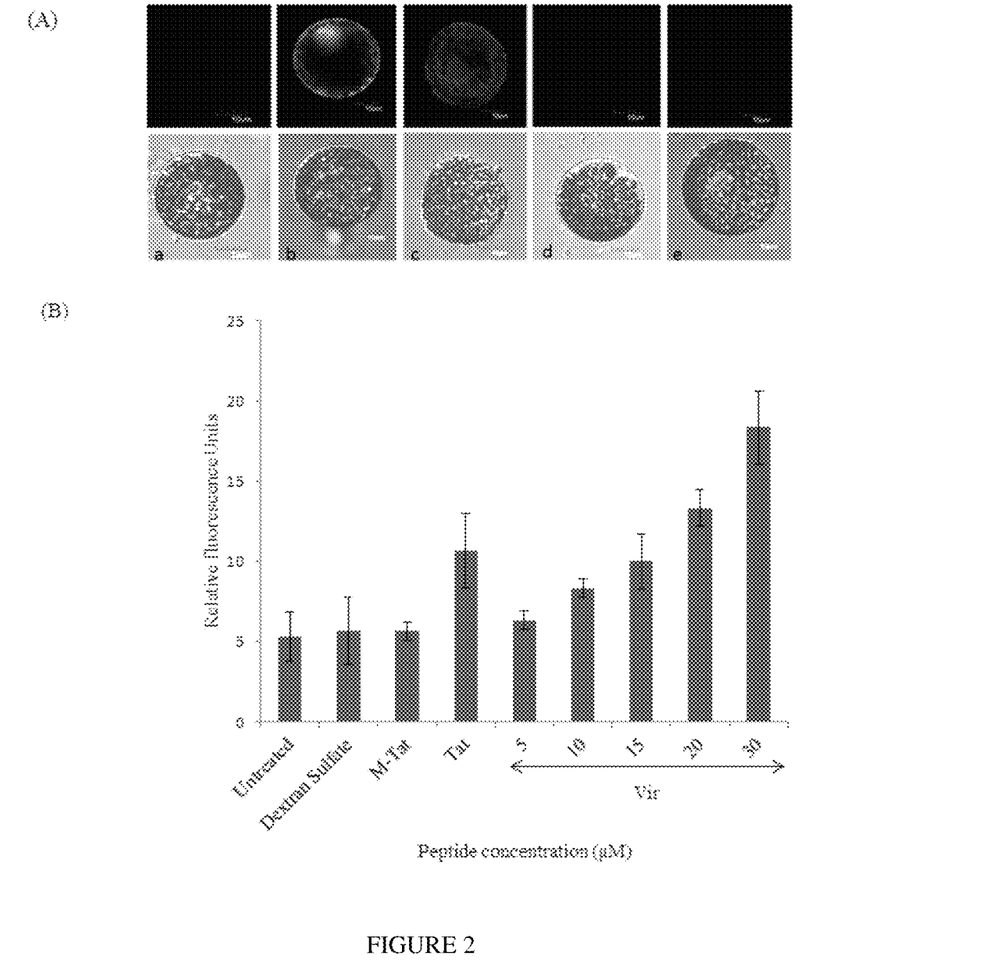
FIG. 2: illustrates the cellular internalization of FITC-Vir in mesophyll protoplasts of *T. aestivum* (A) Confocal microscopic images of cellular uptake (a) untreated (No peptide) (b) Vir (15 µM) (c) Tat (5 µM) (d) M-Tat (5 µM) (e) Dextran Sulphate (5 µM). (B) Quantitative estimation of uptake in protoplasts as assessed by fluorimetry.

FIG. 2 illustrates that in case of protoplasts, the uptake of Vir is affected in the presence of either endocytic inhibitors. However, in case of HeLa cells, it is observed that the cellular uptake of Vir in HeLa cells is reduced by 20% at 4° C. as well as in presence of chlorpromazine while it remained unaffected in presence of other inhibitors.

As the concentration of peptide increases further to 30 μM, the number of cells exhibiting uptake reach up to ~85%. The viability of the protoplasts is affected at higher concentrations of the peptide, as a drop of 20-30% at 15 μM and 60-70% at 30 μM in the percentage of viable cells is observed with respect to untreated cells (viability 90%). A prominent nuclear localization of the peptide is observed from 15 μM and also the viability of protoplasts is maintained significantly, therefore 15 μM is chosen as the optimum concentration, at which peptide displays sufficient uptake and minimal cytotoxicity to cells.

In another embodiment, a method of targeting and delivering macromolecules to a meristematic tissue that is, root tips and leaf bases, of *T. aestivum*(wheat plant) using the agrobacterium derived cell penetrating peptide nanocarrier Vir includes incubating the meristematic tissues that is, root tips and leaf bases, of *T. aestivum* with the peptide nano-carrier.

Figure 3:
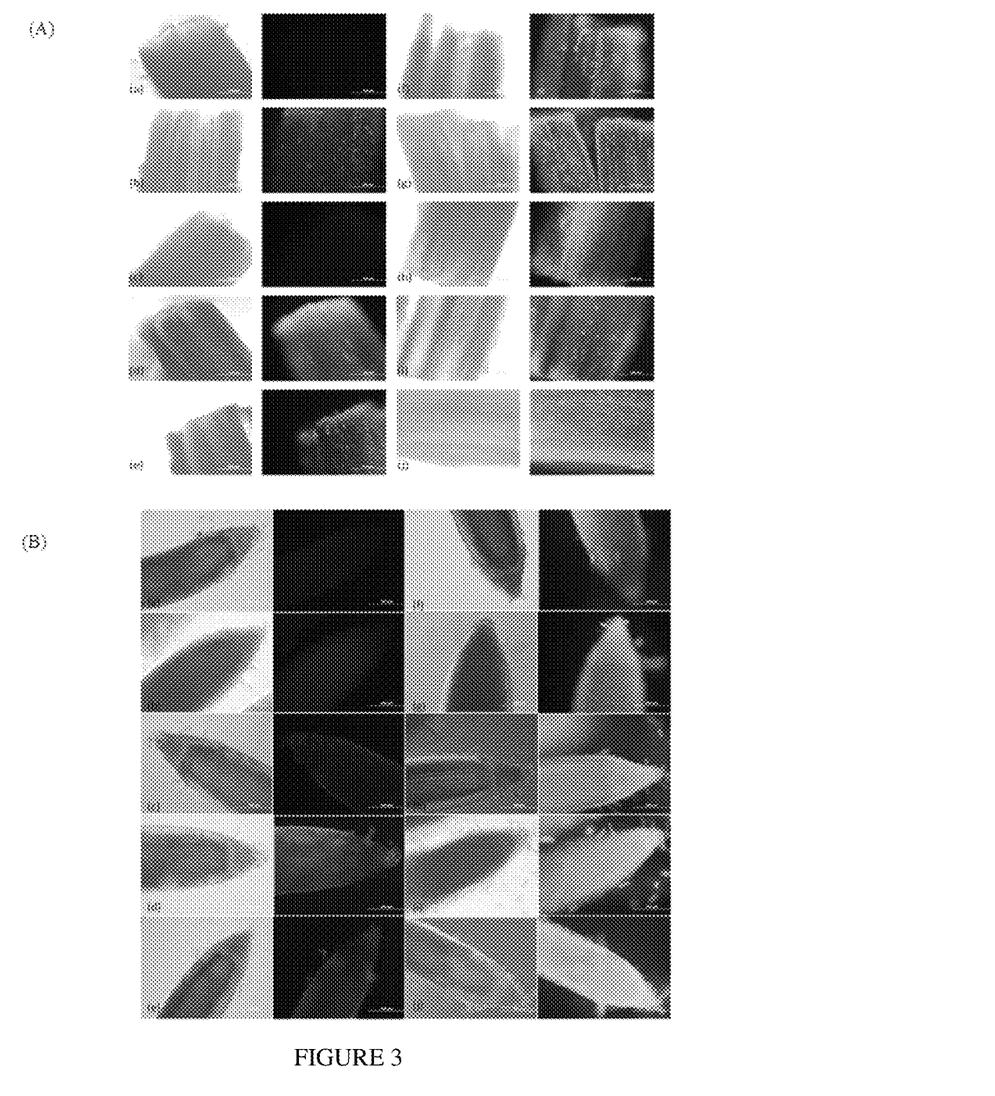
FIG. 3: illustrates the translocation of Vir in various tissues of *T. aestivum* (A) leaf bases (B) root tips. Different panels represent (a) Untreated (b) Dextran sulphate (5 µM) (c) M-Tat (5 µM) (d) Tat (5 µM) (e) Vir: 5 µM (f) 10 µM (g) 15 µM (h) 20 µM (i) 30 µM (j) 40 µM.

In the said embodiment, a process for identification of optimum concentration of the peptide nanocarrier in the meristematic tissues of *T. aestivum* is substantially the same as identification of optimum concentration of the nano-carrier Vir in the mesophyll protoplasts of *T. aestivum* as discussed above and is illustrated in FIG. 3. It is observed that similar to protoplasts, the uptake in the tissues increases with increasing concentration of the peptide.

In some embodiments, the said peptide nanocarrier is used in a peptide-based delivery method for efficient translocation of macromolecules such as proteins, plasmid DNA, siRNA, mRNA, and therapeutic agents inside a mammalian cell.

In one such embodiment, a method of targeting and delivering macromolecules to HeLa cells, as representative of mammalian system, using the peptide nanocarrier includes incubating the HeLa cells with the agrobacterium derived cell penetrating peptide nanocarrier Vir.

Figure 4:
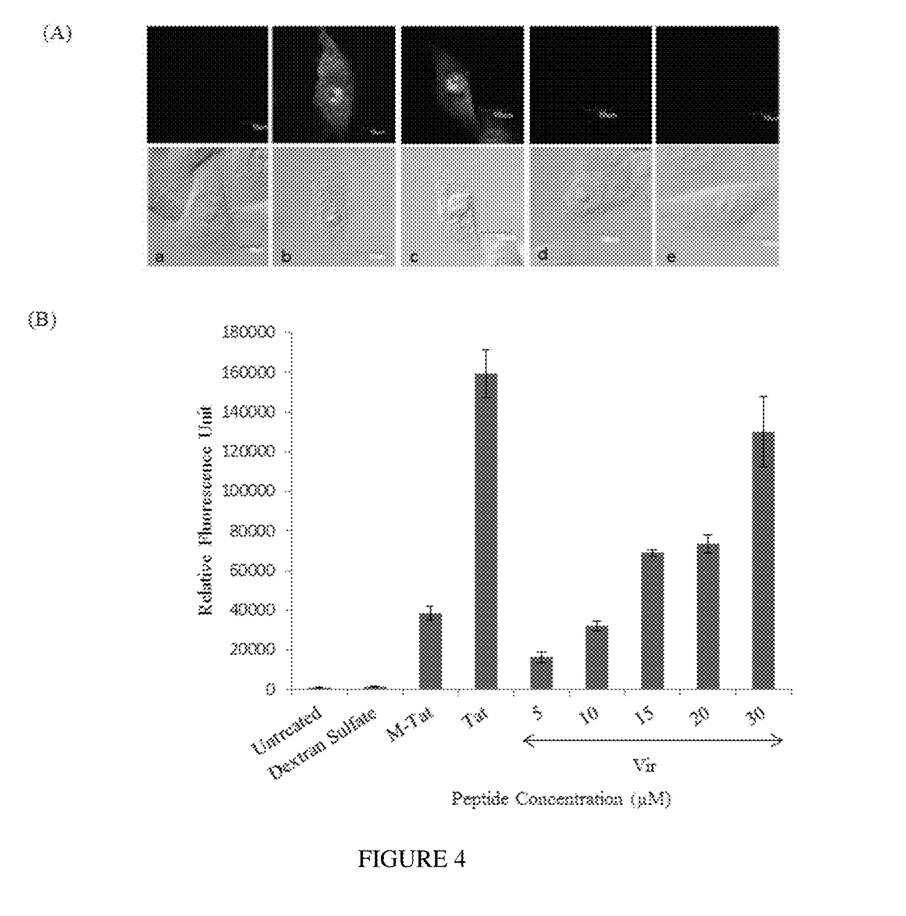
FIG. 4: illustrates the cellular translocation of FITC-Vir in HeLa cells (A) confocal microscopy (a) Untreated (b) Vir (15 µM) (c) Tat (5 µM) (d) M-Tat (5 µM) (e) Dextran Sulphate (5 µM). (B) Quantitative estimation of uptake in HeLa cells as assessed by flow cytometry.

In the said embodiment, a process for identification of optimum concentration of the nano-carrier Vir in the HeLa cells is substantially the same as identification of optimum concentration of the nano-carrier Vir in the mesophyll protoplasts of *T. aestivum* as discussed above and is illustrated in FIG. 4. It is observed that the internalization in HeLa cells starts from 5 µM but a distinct nuclear localization is observed from 15 µM onwards as shown in FIG. 4. As observed with protoplasts, the peptide uptake in HeLa cells also increases with increasing concentration of peptide with 60-70% cells showing uptake at 15 µM and more than 90% cells showing uptake at 30 µM. However, unlike protoplasts, the viability of HeLa cells is not compromised greatly as 94% cells remained viable at 15 µM and 84% cells at 30 µM. Since significant nuclear localization and cellular uptake with minimal loss of viability is observed at 15 µM, therefore, it is chosen as the optimum concentration, at which peptide displays sufficient uptake and minimal cytotoxicity to cells.

According to aspects of the invention, methods of testing the performance in use and properties of the peptide nanocarrier are described in the sections below.

Figure 5:
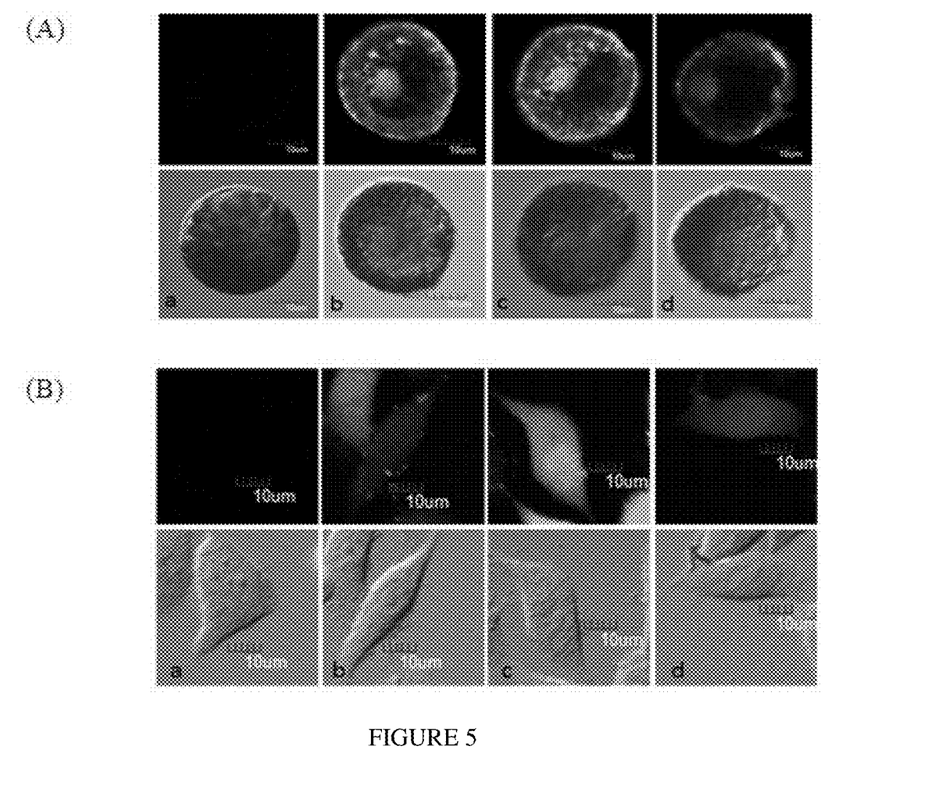
FIG. 5: illustrates the comparison between cellular uptake of mutated Vir and parent Vir peptide. Internalization of mutated Vir in (A) Protoplast and (B) HeLa cells where (a) untreated (b) Vir (15 µM) (c) M-Vir1 (15 µM) (d) M-Vir2 (15 µM).

In an embodiment, in order to understand whether the two NLS sequences "KRPR" and "RKRAR" (SEQ ID NOS 1 and 7, respectively) are able to exhibit CPP activity individually, mutated versions of VirD2 peptides which are discussed above (M-Vir1 (mutation in "KRPR" (SEQ ID NO: 1)-"KAPA" (SEQ ID NO: 8)) and M-Vir2 (mutation in "RKRAR" (SEQ ID NO: 7)-"RKAAA" (SEQ ID NO: 9))), the uptake of mutated Vir(s) is compared with the parent peptide in both the pant and mammalian cellular systems, that is, protoplasts and HeLa cells and is illustrated in FIG. 5. It is observed that CPP activity of M-Vir1 and M-Vir2 is not affected rather the activity of M-Vir1 increased while the activity of M-Vir2 remains similar to the parent peptide.

Figure 6:
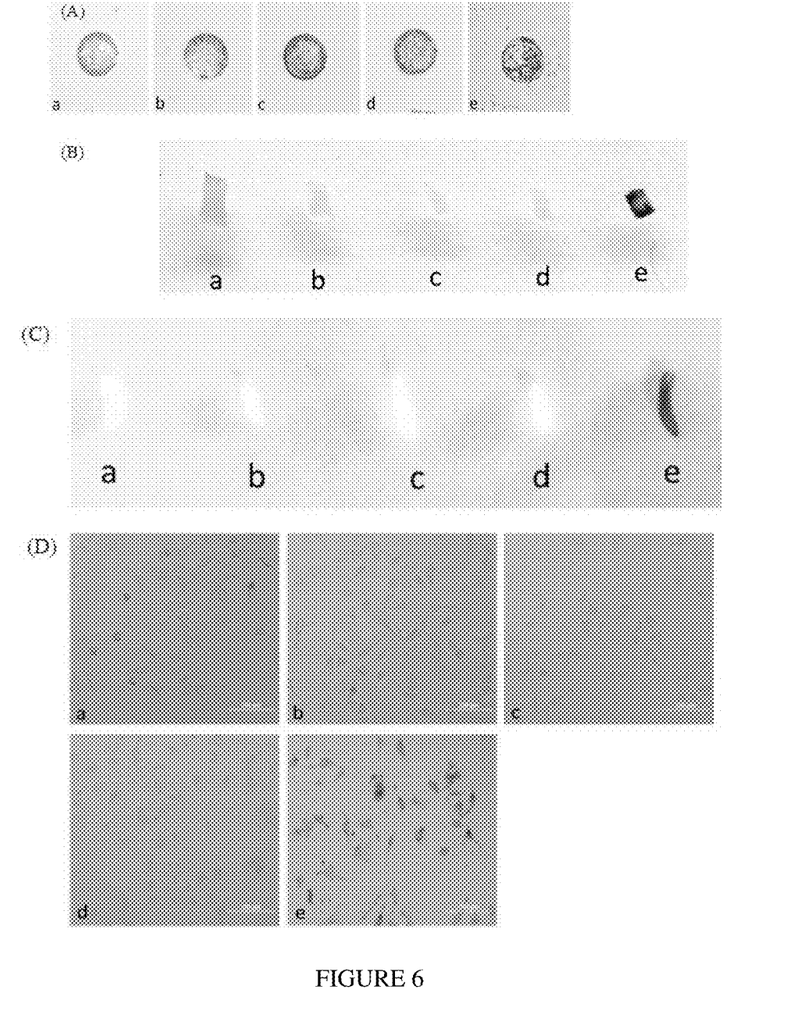
FIG. 6: illustrates an analysis of cargo delivery ability of Vir peptide in plant and mammalian systems. Macromolecule delivery by Vir in (A) Protoplast of wheat (B) leaf bases (C) root tips with (a) no peptide (b) GUS buffer only (c) β-glucuronidase only (d) Vir only (e) Vir-β-galactosidase; (D) HeLa cells with (a) non peptide (b) X-gal staining solution only (c) β-galactosidase only (d) Vir only (e) Vir-β-galactosidase.

In one embodiment, the ability of the peptide nanocarrier to deliver macromolecular cargoes in cells is evaluated by using β-glucuronidase enzyme as the reporter protein whereas β-galactosidase is employed for delivery in mammalian cells. The reporter proteins are non-covalently complexed with peptide nanocarrier, SEQ ID NO: 3 with the sequence KRPRRKRARGNRR at room temperature for 1 hr. The reporter proteins are used at a concentration of 1 µg while the peptide nanocarrier is used at the optimized concentration that is, 15 µM for complex formation. The peptide-protein complexes thus formed, were incubated with mammalian cells, plant protoplasts and tissues (root tips and leaf bases) further for 1 hour at 18-37 deg C. and room temperature, at pH range from 5.5 to 7.5 respectively. The enzyme delivery by peptide nanocarrier is examined by staining the cells with respective staining solutions. The appearance of blue colour in cells confirms the delivery of the reporter protein. FIG. 6 illustrates macromolecule delivery by Vir (as discussed in said embodiments) in (A) Protoplast of wheat (B) leaf bases (C) root tips with (a) no peptide (b) GUS buffer only (c) β-glucuronidase only (d) Vir only (e) Vir-β-galactosidase; (D) HeLa cells with (a) non peptide (b) X-gal staining solution only (c) β-galactosidase only (d) Vir only (e) Vir-β-galactosidase. It is found that the delivery efficiency of the nanocarrier Vir in root tips and leaf bases corresponded to 90% while in protoplasts it was 50% (FIG. 6 A-C). The nanocarrier Vir is able to deliver the enzyme β-galactosidase with more than 90% efficiency in HeLa cells (FIG. 6 D). Controls show no appearance of blue colour which further confirms the role of Vir in macromolecular delivery in both plant and animal cells.

Figure 7:
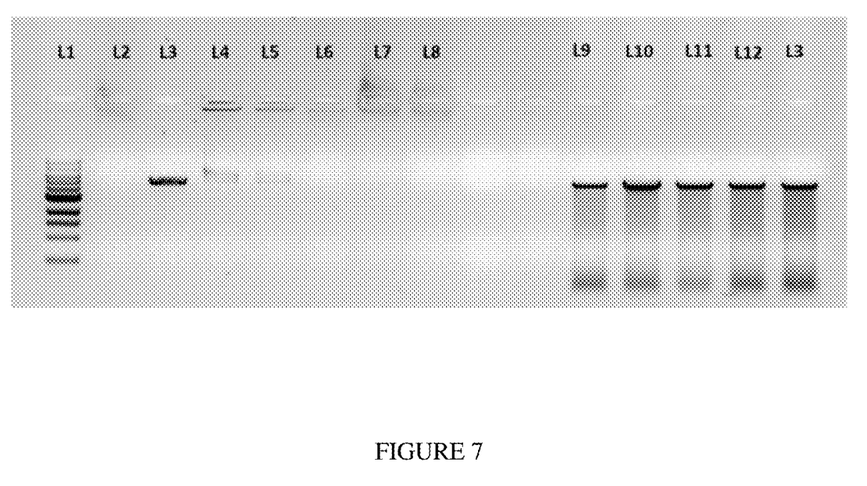
FIG. 7: illustrates an assessment of DNA binding and protection ability of Vir peptide. Gel retardation assay of plasmid DNA, pEGFP-N1 upon complexation with Vir peptide: L1, 1 kb DNA ladder; L2, Vir only; L3, DNA only; L4, DNA: Vir (1:0.5); L5, 1:1; L6, 1:2; L7, 1:3; L8, 1:4.DNaseI protection assay to analyse extent of degradation of DNA by enzyme DNaseI: L9, DNA: Vir, 1:0.5; L10, 1:1; L11, 1:2; L12, 1:3; L13, 1:4.

In one embodiment, DNA binding and protection ability of the peptide nanocarrier is described and is illustrated with the help of FIG. 7, which illustrates gel retardation assay of plasmid DNA, pEGFP-N1 upon complexation with Vir peptide: L1, 1 kb DNA ladder; L2, Vir only; L3, DNA only; L4, DNA: Vir (1:0.5); L5, 1:1; L6, 1:2; L7, 1:3; L8, 1:4.DNase I protection assay to analyse extent of degradation of DNA by enzyme DNase I: L9, DNA: Vir, 1:0.5; L10, 1:1; L11, 1:2; L12, 1:3; L13, 1:4. Vir carries a net charge of +9 units, therefore its DNA binding and protection ability is established. The peptide-DNA complex are formed by combining several w/w ratios of peptide:DNA, keeping the weight of DNA constant. It is observed that the peptide-DNA complex sticks to the wells at the lowest ratio 0.5:1 onwards and starts migrating in the opposite direction at ratios 1:3 and 1:4.

In one embodiment, DNA protection ability of the nano-carrier Vir is also described. In such embodiments, the Vir-peptide-DNA complex is treated with DNase I enzyme. It is observed that DNA bands are present at all ratios of peptide-DNA complex (0.5:1 to 4:1) suggesting that Vir shows DNase protection ability from as low as 0.5:1 ratio (peptide:DNA). Combined with its nuclear localization and efficient DNA binding ability, the nanocarrier Vir can be used as a carrier for studying gene function and gene manipulation in vivo.

In one embodiment, the peptide nanocarrier displays anti-microbial activity that is, it kills/inhibits the growth of microorganisms, thereby further increasing its utility in development of antimicrobial agents against various pathogens. The said nanocarrier demonstrate efficient targeting and delivering macromolecules to cells (protoplasts as well as tissues) in a simple, one-step mechanism.

Figure 8:
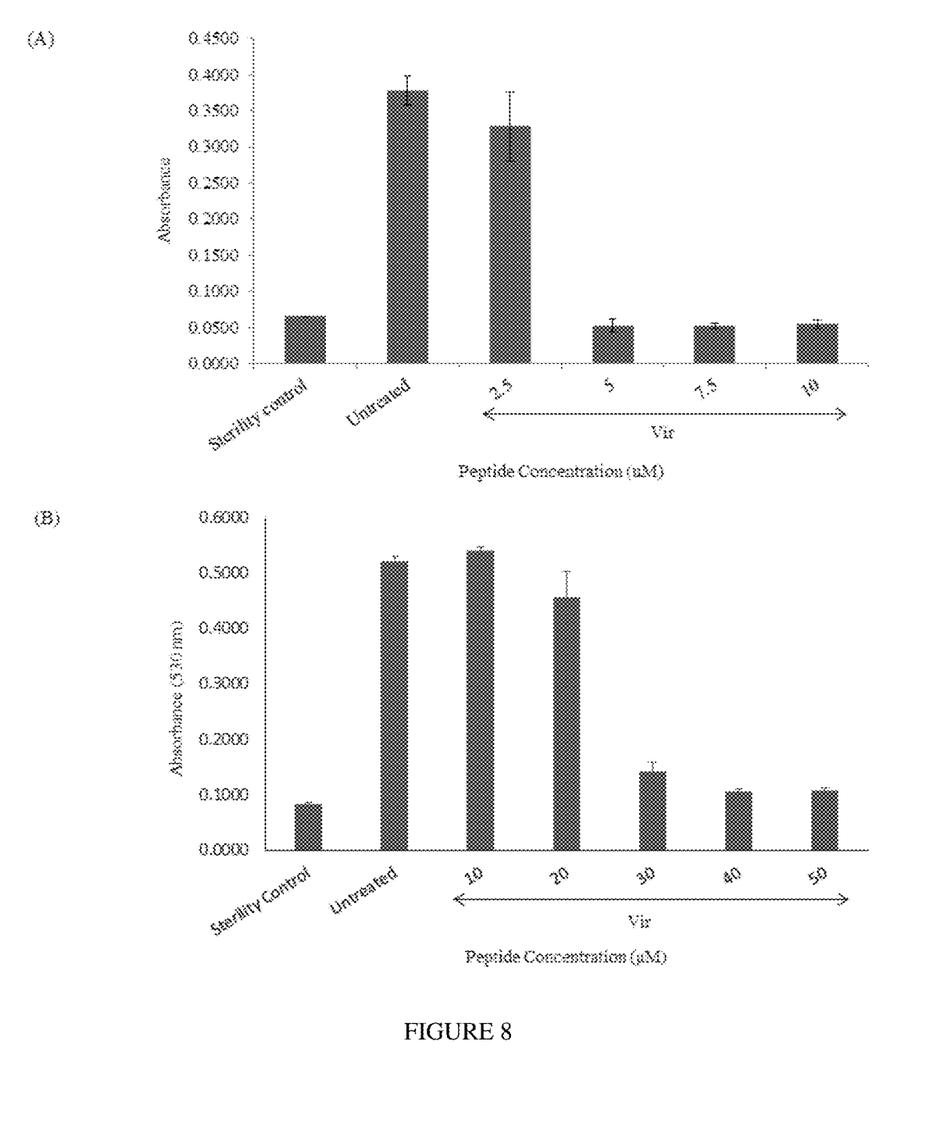
FIG. 8: illustrates an antimicrobial activity of Vir as determined against (A) *X. oxanopodus* and (B) *F. solani*

In one embodiments, a method of evaluating antimicrobial activity of the nanocarrier Vir against bacterial and fungal plant pathogens namely Xanthomonasoxanopodus and Fusariumsolani, respectively is also described and is illustrated in FIG. 8. The lowest concentration at which the isolates are completely inhibited (as evidenced by the absence of visible growth) is recorded as the minimal inhibitory concentration or MIC. A concentration gradient of 0-50 µM is tested against both the organisms and it is found that a complete inhibition in the growth of X. oxanopodusis observed at 5 µM, while a concentration of 30 µM of Vir peptide is effective against *F. solani*). The ability of the nano-carrier Vir to translocate itself across the plasma membrane without disrupting it and to kill the pathogenic agents at the same time can be useful in controlling these pathogens in the infected host.

Advantages

1. The present invention establishes a novel peptide-based vector for efficiently targeting and delivering macromolecules to cells (protoplasts as well as tissues) in a simple, one-step mechanism.
2. The present invention enables delivery of non-covalently as well as covalently linked macromolecules such as drugs to cells.
3. The present invention localizes specifically in the nucleus and efficiently binds to DNA molecules in vitro, thereby providing a plausible system for gene delivery to the cells for applications in human therapeutics and generation of transgenics.
4. The present invention is cost-effective, since it requires synthesis of only one peptide in comparison to currently available complex delivery systems.
5. The present invention also possesses antimicrobial activity against common bacterial and fungal pathogens, thereby, minimizing infection of cells during the process of transgenic generation.

Although the embodiments herein are described with various specific embodiments, it will be obvious for a person skilled in the art to practice the embodiments herein with modifications. However, all such modifications are deemed to be within the scope of the invention. It is also to be understood that the description is intended to cover all of the generic and specific features of the embodiments described herein and all the statements of the scope of the embodiments which as a matter of language might be said to fall there between.

We claim:

1. A peptide nanocarrier sequence selected from the group consisting of SEQ ID NO: 3, SEQ ID NO: 4 and SEQ ID NO: 5.

2. The peptide nanocarrier sequence according to claim 1, wherein said sequence forms a complex with a macromolecule.

3. The peptide nanocarrier sequence according to claim 1, wherein said macromolecule is selected from the group comprising of a peptide, a polypeptide, or a protein, a polysaccharide, a lipid, a lipoprotein, a glyco lipid, a nucleic acid, a drug molecule or a toxin or an imaging or contrast agent.

4. The peptide nanocarrier sequence as according to claim 1, wherein said peptide nano carrier has a positive charge of +9 units.

5. The peptide nanocarrier sequence according to claim 1, wherein said peptide nano carrier possesses antimicrobial activity.

6. A method for cellular delivery, comprising the steps of:
   a) complexation of a peptide nanocarrier sequence selected from the group
   consisting of SEQ ID NO: 3, SEQ ID NO: 4 and SEQ ID NO: 5 with a macromolecule to obtain a complex;
   b) administering the complex in the concentration range of 0.1 uM to 50 uM to a targeted mammalian or plant cell or tissue at predetermined pH and temperature conditions.

7. The method according to claim 6, wherein said predetermined conditions are pH in range of 5.5-7.5 and temperature in the range of 18-37 degrees.

8. The method as according to 6, wherein said macromolecule is selected from a group comprising of a peptide, a polypeptide, or a protein, a polysaccharide, a lipid, a lipoprotein, a glyco lipid, a nucleic acid, a small drug molecule or a toxin, a nanoparticle and an imaging or contrast agent.

* * * * *